(12) United States Patent
Ohkawa et al.

(10) Patent No.: US 11,414,680 B2
(45) Date of Patent: Aug. 16, 2022

(54) METHOD FOR INSERTING DESIRED DNA FRAGMENT INTO SITE LOCATED ADJACENT TO BINDING DOMAIN OF DNA-BINDING PROTEIN

(71) Applicant: KYUSHU UNIVERSITY, NATIONAL UNIVERSITY CORPORATION, Fukuoka (JP)

(72) Inventors: Yasuyuki Ohkawa, Fukuoka (JP); Akihito Harada, Fukuoka (JP); Hitoshi Kurumizaka, Yokohama (JP); Hiroshi Kimura, Yokohama (JP); Tetsuya Handa, Yokohama (JP); Yuko Sato, Yokohama (JP); Yoko Hayashi, Osaka (JP)

(73) Assignee: KYUSHU UNIVERSITY NATIONAL UNIVERSITY CORPORATION, Fukuoka (JP)

( * ) Notice: Subject to any disclaimer, the term of this patent is extended or adjusted under 35 U.S.C. 154(b) by 614 days.

(21) Appl. No.: 16/327,754

(22) PCT Filed: May 24, 2017

(86) PCT No.: PCT/JP2017/019309
§ 371 (c)(1),
(2) Date: Apr. 16, 2019

(87) PCT Pub. No.: WO2018/042776
PCT Pub. Date: Mar. 8, 2018

(65) Prior Publication Data
US 2020/0010853 A1 Jan. 9, 2020

(30) Foreign Application Priority Data
Aug. 30, 2016 (JP) .............................. JP2016-167967

(51) Int. Cl.
*C12N 15/87* (2006.01)
*C12Q 1/6806* (2018.01)
(52) U.S. Cl.
CPC ........... *C12N 15/87* (2013.01); *C12Q 1/6806* (2013.01)
(58) Field of Classification Search
None
See application file for complete search history.

(56) References Cited

U.S. PATENT DOCUMENTS

| 2006/0258603 A1 | 11/2006 | Ivics et al. |
| 2012/0164689 A1 | 6/2012 | Fujii et al. |
| 2018/0335424 A1* | 11/2018 | Chen .................... C12Q 1/6869 |

FOREIGN PATENT DOCUMENTS

| WO | WO-2010048605 A1 | 4/2010 |
| WO | WO-2013078470 A2 | 5/2013 |
| WO | WO-2014189957 A2 | 11/2014 |
| WO | WO-2014190214 A1 | 11/2014 |
| WO | WO-2014205296 A1 | 12/2014 |

OTHER PUBLICATIONS

Sos, B.C. et al., Characterization of chromatin accessibility with a transposome hypersensitive sites sequencing (THS-seq) assay, Genome Biol., vol. 17:20, pp. 1-15 (Year: 2016).*
International Search Report issued in PCT/JP2017/019309 dated Aug. 15, 2017.
Carey, et al., Chromatin Immunoprecipitation (ChIP), Cold Spring Harbor Laboratory Press, 2009, 4:9:1-8.
Gilfillan et al, Limitations and possibilities of low cell number ChIP-seq, BMC Genomics, Biomed Central, 2012, 13:1:645, 13 pages.
Extended European Search Report issued in EP17845787 dated Feb. 19, 2020.
Extended European Search Report issued in EP17845787 dated Mar. 2, 2020.

* cited by examiner

*Primary Examiner* — Teresa E Strzelecka
(74) *Attorney, Agent, or Firm* — Blank Rome LLP (57) ABSTRACT

A method is provided for integrating a DNA fragment of a desired base sequence into a site located adjacent to a binding region of a DNA-binding protein bound to a DNA molecule, the method including bringing the DNA fragment having a base sequence including a transposase-binding sequence and the desired base sequence close to the binding region using a specific binding substance to the DNA-binding protein, binding transposase to the transposase-binding sequence, and activating the transposase such that the DNA fragment of the desired base sequence is integrated into the site located adjacent to the binding region.

8 Claims, 7 Drawing Sheets

Specification includes a Sequence Listing.

METHOD FOR INSERTING DESIRED DNA FRAGMENT INTO SITE LOCATED ADJACENT TO BINDING DOMAIN OF DNA-BINDING PROTEIN

TECHNICAL FIELD

The present invention relates to a method for integrating a desired DNA fragment into a site located adjacent to a binding region of a DNA-binding protein. Priority is claimed on Japanese Patent Application No. 2016-167967, filed on Aug. 30, 2016, the content of which is incorporated herein by reference.

BACKGROUND ART

As a method for detecting binding between a protein and a specific genome domain, or interaction between genome domains, chromatin immunoprecipitation (CHIP) analysis, ChIP-chip analysis, ChIP-Seq analysis, Chromosome Conformation Capture (3C, Hi-C), and the like are widely used (for example, refer to NPL 1).

These methods are generally performed as follows. First, DNA and a DNA-binding protein are crosslinked by UV irradiation, formaldehyde treatment, and the like, and then DNA fragments are obtained by ultrasonication, restriction enzyme treatment, and the like. Subsequently, the DNA fragments bound to the DNA-binding proteins are collected by immunoprecipitation. After the DNA-binding proteins are removed from the collected DNA fragments by proteasce treatment, a base sequence of the DNA fragment is analyzed by dot blot hybridization or southern hybridization using radiation labeling probe, hybridization of DNA array (ChIP-chip analysis), PCR, real-time PCR, base sequence analysis using next-generation sequencer (ChIP-Seq analysis), and the like.

CITATION LIST

Non-Patent Literature

[NPL 1] Carey M. E. et al., Chromatin Immunoprecipitation (ChIP), Cold Spring Harbor Protocols, 4(9), pdb. prot5279, 2009.

SUMMARY OF INVENTION

Technical Problem

However, for example, insoluble proteins cannot be used for immunoprecipitation. In addition, in a case where a sample is a small number of cells and the like, a carrier is required to be used at the time of reaction, and thus mixing of impurities or loss of a target is inevitable. For this reason, in the conventional method in which immunoprecipitation is an essential step, there was a case where analysis of binding of insoluble proteins to DNA or analysis from a small number of cells such as tissues was difficult. Here, an object of the present invention is to provide a technique capable of analyzing binding between a protein and a specific genome domain without performing immunoprecipitation.

Solution to Problem

The present invention includes the following aspects.

(1) A method for integrating a DNA fragment of a desired base sequence into a site located adjacent to a binding region of a DNA-binding protein bound to a DNA molecule, the method including a step of bringing the DNA fragment having a base sequence including a transposase-binding sequence and the desired base sequence close to the binding region using a specific binding substance to the DNA-binding protein, a step of binding a transposase to the transposase-binding sequence, and a step of activating the transposase such that the DNA fragment of the desired base sequence is integrated into the site located adjacent to the binding region.

(2) The method according to (1), further including a step of performing gene amplification of the DNA molecule using the desired base sequence as a starting point to obtain an amplification product and a step of analyzing a base sequence of the amplification product.

(3) The method according to (2), in which the desired base sequence includes a promotor sequence, the gene amplification is performed by bringing RNA polymerase into contact with the promotor sequence and transcribing DNA downstream the promotor sequence to generate RNA.

(4) The method according to (3), in which the desired base sequence further includes an identification sequence downstream the promotor sequence.

(5) A bonded body of a DNA fragment having a base sequence including a transposase-binding sequence and a desired base sequence, and a specific binding substance to a DNA-binding protein or a specific binding substance to the specific binding substance.

(6) The bonded body according to (5), in which the desired base sequence includes a promotor sequence.

(7) The bonded body according to (6), in which the desired base sequence further includes an identification sequence downstream the promotor sequence.

Advantageous Effects of Invention

According to the present invention, it is possible to provide a technique capable of analyzing binding between a protein and a specific genome domain without performing immunoprecipitation. Therefore, for example, it is possible to analyze binding of a protein such as insoluble proteins, of which immunoprecipitation is difficult to be performed, to DNA.

DESCRIPTION OF EMBODIMENTS

Hereinafter, referring to figures depending on the case, embodiments of the present invention will be described in detail. In the figures, like or corresponding parts have like or corresponding reference signs, and overlapping description will not be repeated. In addition, the dimension ratio in each figure can be exaggerated for explanation and does not necessarily coincide with the actual dimension ratio.

[Method for Integrating Desired DNA Fragment Located into Site Adjacent to Binding Region of DNA-Binding Protein]

In Example 1, the present invention is a method for integrating a DNA fragment of a desired base sequence into a site located adjacent to a binding region of a DNA-binding protein bound to a DNA molecule, the method including a step (a) of bringing a DNA fragment having a base sequence including a transposase-binding sequence and the desired base sequence close to the binding region using a specific binding substance to the DNA-binding protein, a step (b) of binding transposase to the transposase-binding sequence, and a step (c) of activating the transposase, and as a result, integrating a DNA fragment of the desired base sequence into a site adjacent to the binding region. Hereinafter, the method of this embodiment is sometimes referred to as a Chromatin Integration Labeling Technology (ChILT) method.

As described above, insoluble proteins cannot be used for immunoprecipitation. In addition, for example, immunostaining of immobilized tissues or cells can stain a wide range of protein, while antigens that can be collected by immunoprecipitation are limited, and only approximately 10% of antigens that can be immunostained can be immunoprecipitated. In addition, in immunoprecipitation where a sample is a small number of cells and the like, a carrier is required to be used, and thus there is a problem in the mixing of impurities and/or the loss of a target. By contrast, according to the ChILT method, it is possible to analyze binding between a protein and a specific genome domain without performing immunoprecipitation.

Therefore, according to the ChILT method, regarding the DNA-binding protein of which analysis was difficult by the conventional technology which includes immunoprecipitation as an essential step, it is possible to analyze bonding between the DNA-binding protein and DNA. In addition, in the conventional techniques, it was difficult to perform analysis of a DNA-binding protein at single-cell level. With respect to this, according to the ChILT method, as described to be later, it is also possible to perform analysis of a DNA-binding protein at single-cell level.

The DNA-binding protein to be an analysis target is not particularly limited, and examples thereof include histone, transcription factor, phosphorylated polymerase, and the like. For example, by analyzing RNA polymerase II in a specific phosphorylated state as a DNA-binding protein, it is possible to analyze a transcription state of a gene.

Figure 1A:
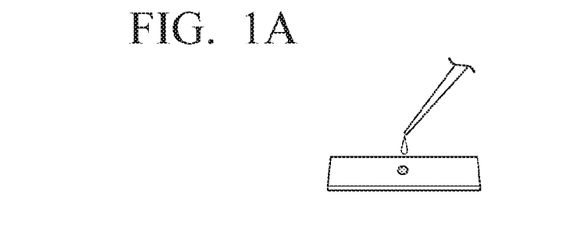
FIG. 1A is a schematic view showing a Chromatin Integration Labeling Technology (ChILT) method.
Figure 1B:
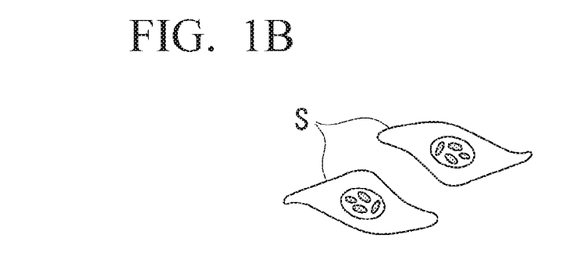
FIG. 1B is a schematic view showing the ChILT method.
Figure 1C:
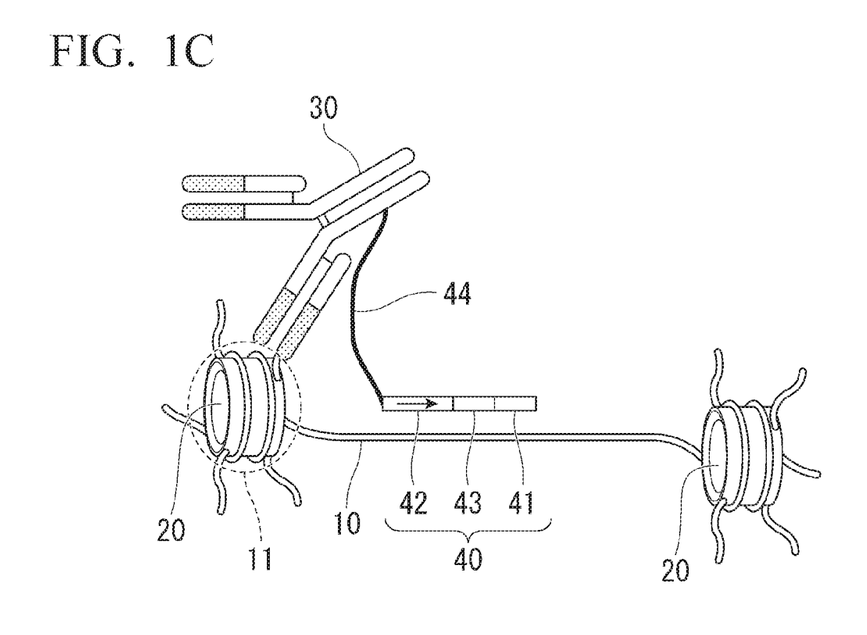
FIG. 1C is a schematic view showing the ChILT method.

Hereinafter, the ChILT method is described referring FIG. 1A to FIG. 5. FIG. 1A to FIG. 5 are schematic views showing the ChILT method. FIG. 1A is a view showing a paraformaldehyde-immobilized cell specimen. FIG. 1B is an enlarged view of a cell specimen S immobilized on a slide glass of FIG. 1A. FIG. 1C is a view showing reaction occurring in a nucleus of the cell specimen S in a case where the ChILT method is performed on the cell specimen S. FIG. 1C shows a state in which a genome DNA 10 is wound around a histone 20 to form a chromatin structure. In the example of FIG. 1C, the DNA-binding protein is the histone 20.

In the example of FIG. 1C, a specific binding substance 30 is an antibody recognizing the histone 20. The specific binding substance 30 is bound to a DNA fragment 40 via a linker 44. The DNA fragment 40 has a base sequence including a transposase-binding sequence 41 and a desired base sequence. In examples of FIGS. 1A to 1C, the desired base sequence is a base sequence in which an identification sequence 43 is linked downstream a T7 promotor sequence 42. In FIG. 1C to FIG. 6, arrows of the T7 promotor sequence 42 indicate a direction of transcription by T7 polymerase.

The linker 44 has a role of a tie (tether) for bringing the DNA fragment 40 close to a binding region 11 of the histone 20. In the example of FIG. 1C, the linker 44 is a DNA fragment, and for example, has a length of 50 to 70 bases. However, the linker 44 is not particularly limited as long as the linker functions as a tether, and may be made of a polymer such as polyethylene glycol.

(Step (a))

In the example of FIG. 1C, the ChILT method is performed using a paraformaldehyde-immobilized cell specimen S as a sample. First, the DNA fragment 40 and the binding region 11 are brought close to each other by using the specific binding substance 30 to the histone 20. Here, bringing the two close to each other by using the specific binding substance 30 may be bringing the DNA fragment 40 and the binding region 11 close to each other by binding the specific binding substance 30 bound to the DNA fragment 40 with the histone 20 which is an antigen thereof as in the example of FIG. 1C. Alternatively, the specific binding substance 30 is a mouse IgG antibody to the histone 20, and the mouse IgG antibody is bound to the histone 20 as a primary antibody, subsequently, an anti-mouse IgG antibody bound to the DNA fragment 40 is bound to the primary antibody as a secondary antibody, and thus the DNA fragment 40 and the binding region 11 may be brought close to each other.

The step of bringing the DNA fragment 40 and the binding region 11 close to each other by using the specific binding substance 30 to the histone 20 can be performed in a cell of a paraformaldehyde-immobilized tissue section as in the example of FIG. 1C. Similar to immunostaining, in the step, a plurality of antibodies can be also simultaneously used. Therefore, according to the ChILT method, it is possible to integrate different DNA fragments of desired base sequences into sites located adjacent to binding regions of a plurality of DNA-binding proteins. Here, by using a distinguishable sequence per a DNA-binding protein as the identification sequence 43, it is possible to detect the binding of a certain DNA-binding protein to DNA by distinguishing from the bindings of the other DNA-binding proteins to DNA.

(Step (b))

Figure 2:
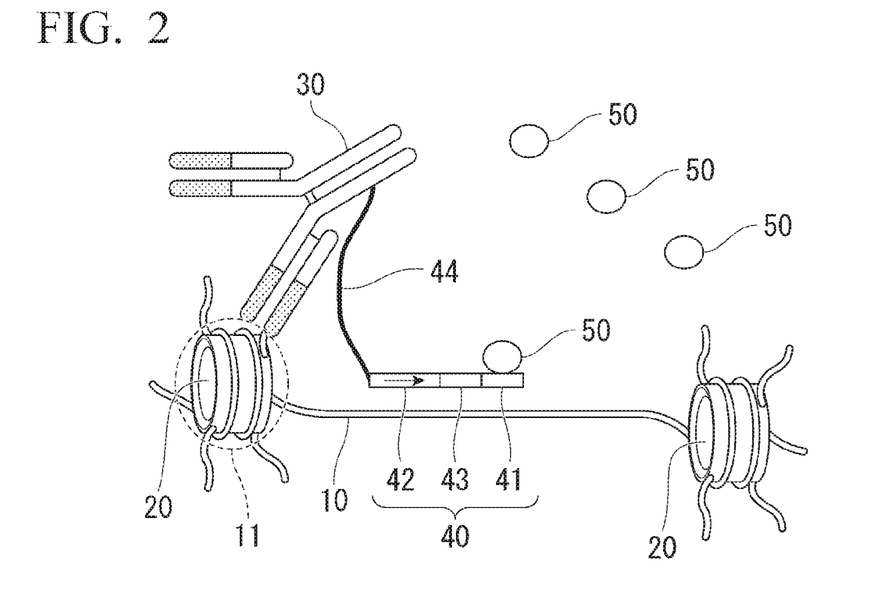
FIG. 2 is a schematic view showing the ChILT method.

Subsequently, a transposase 50 is bound to a transposase-binding sequence 41. FIG. 2 shows a state in which the transposase 50 is added to a sample to bind the transposase 50 to the transposase-binding sequence 41.

As the transposase, from a viewpoint of easy intranuclear transport, a transposase having a small size is preferable. For example, a transposase having a molecular weight of 50 KDa or less is preferable. In addition, a transposase having high sequence specificity of a sequence to be identified is preferable. In addition, a DNA type transposase is preferable. In addition, a transposase capable of controlling activity is preferable. For example, a transposase activated when a cation such as a divalent metal ion is added to a buffer is exemplified. Examples of a preferable transposase include TN5 transposase, sleeping beauty transposase (SB10), TN10, and the like. The transposase-binding sequence 41 may be determined depending on a transposase to be used.

(Step (c))

Subsequently, the transposase 50 is activated. Activation of the transposase 50 can be performed by adding a divalent metal ion to a buffer.

In addition, depending on the kind of the transposase 50, there is a case where a dimer for exhibiting activation of transferring a DNA fragment is required to be formed. In addition, in order for the transposase 50 to form a dimer, there is a case where the transposase 50 is required to be bound to the transposase-binding sequence 41. For example, the TN5, SB10, TN10, and the like are such transposases. In such a case, it is possible to activate the transposase 50 even by forming a dimer of the transposase 50.

In addition, depending on the kind of the transposase 50, in order to activate the transposase 50, there is a case where it is required to form a dimer of the transposase 50 and to add a divalent metal ion to a buffer.

Figure 3:
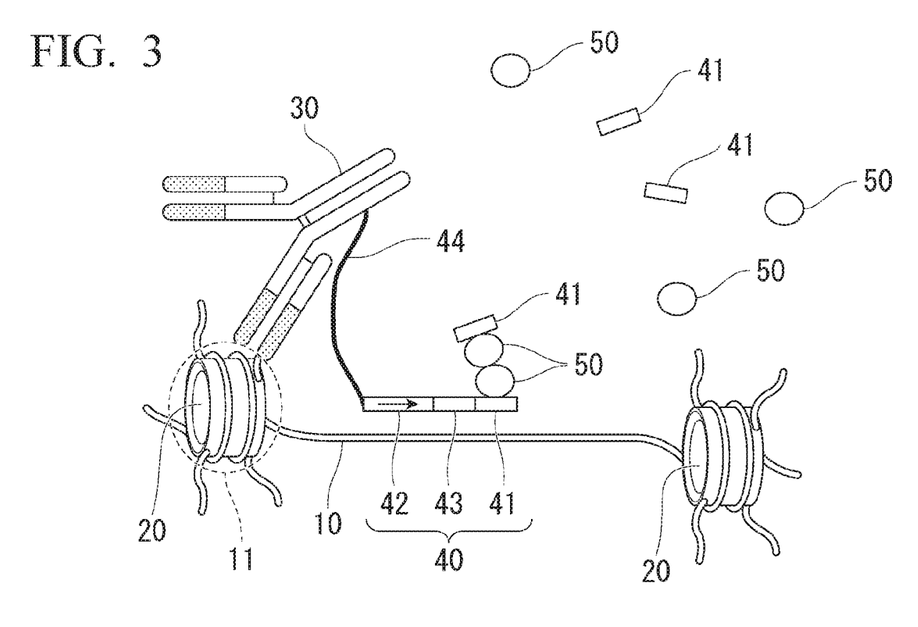
FIG. 3 is a schematic view showing the ChILT method.

FIG. 3 shows a state in which a dimer of the transposase 50 is formed. In FIG. 3, a free DNA fragment having the transposase-binding sequence 41 is added to a sample to bind the transposase 50 to the DNA fragment. As shown in FIG. 3, the transposase 50 bound to the DNA fragment forms a dimer with the transposase 50 bound to the transposase-binding sequence 41 constituting the DNA fragment 40.

As a result of activating the transposase 50, the DNA fragment of a desired base sequence (in the example of FIG. 3, a base sequence to which the identification sequence 43 is linked downstream the T7 promotor sequence 42) in the DNA fragment 40 is integrated into a site adjacent to the binding region 11. Here, the site adjacent to the binding region 11 is preferably a spatially close domain. For example, the site may be equal to or less than 500 bases from the binding region 11, for example, may be equal to or less than 100 bases, and for example, may be equal to or less than 50 bases.

Alternatively, since the site is preferably a spatially close domain, the base sequence of the genome DNA 10 is a domain extremely far from the binding region 11 and may be a domain adjacent thereto by mutual interaction between the genome domains. That is, the base sequence of the genome DNA 10 may be a domain adjacent thereto in terms of the chromosomal structure.

In this step, integration reaction of the DNA fragment is incompletely ended by the transposase 50. Specifically, for example, in a case where the integrated DNA fragment partially becomes one chain DNA, a case where the integrated DNA fragment is fragmented is exemplified. Here, by fill-in reaction using T4 DNA ligase, T4 DNA polymerase I, and the like, a step of completely ending integration reaction of the DNA fragment by the transposase 50 may be further performed.

Figure 4:
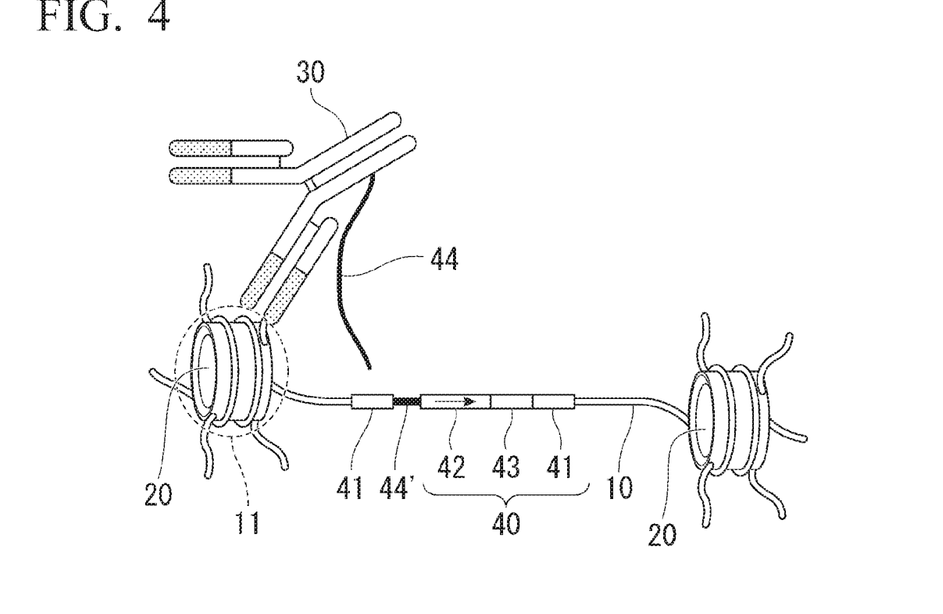
FIG. 4 is a schematic view showing the ChILT method.
Figure 5:
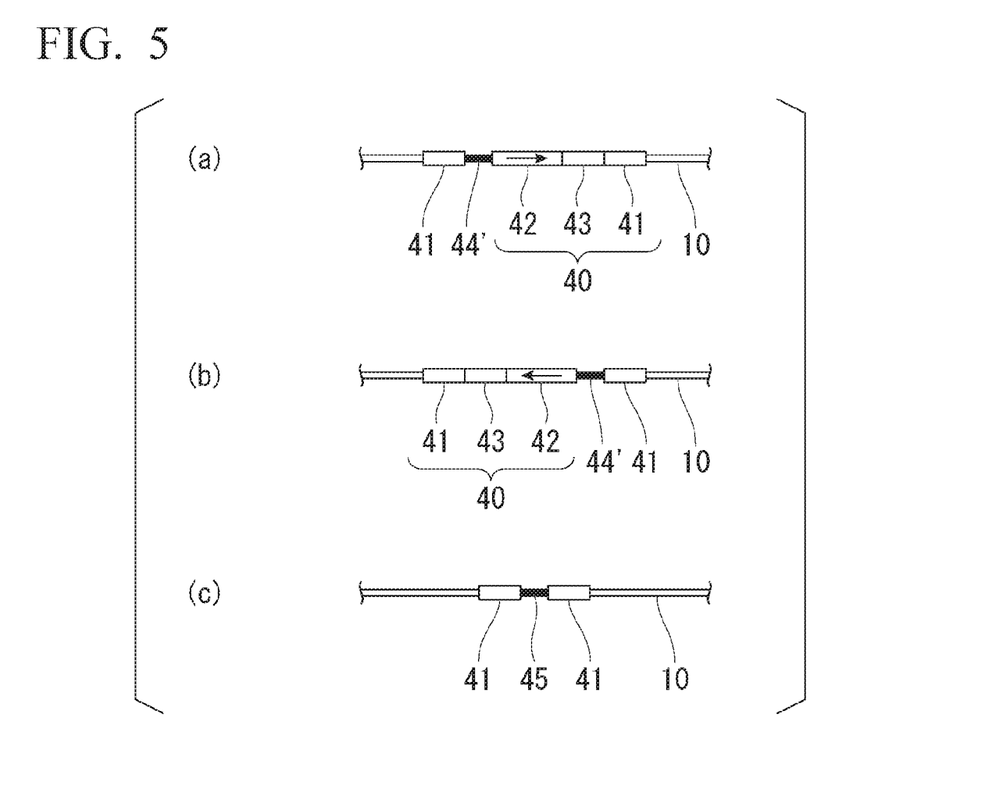
FIGS. 5(a) to 5(c) are schematic views showing the ChILT method.

FIG. 4 is a schematic view showing an example of a state in which the DNA fragment of a desired base sequence is integrated into a site adjacent to the binding region 11. As shown in FIG. 4, in this example, the DNA fragment of a desired base sequence (the base sequence to which the identification sequence 43 is linked downstream the T7 promotor sequence 42) is integrated into a site adjacent to the binding region 11. In the example of FIG. 4, not only the desired base sequence but also two transposase-binding sequences 41 and a base sequence 44' derived from part of the linker 44 are also integrated into the genome DNA 10.

FIG. 5(a) to 5(c) are schematic views showing an example of a case where the DNA fragment is integrated into the genome DNA 10 as a result of activating the transposase 50 from the state of FIG. 3. FIG. 5(a) shows the state of FIG. 4. FIG. 5(b) shows a state in which a desired base sequence is integrated in a reverse direction of the direction of the state of FIG. 4. FIG. 5(c) shows a base sequence that can be integrated into the genome DNA 10 in a case where transposase 50 bound to the free DNA fragment having the transposase-binding sequence 41 forms a dimer.

In FIG. 5(c), there is a case where the base sequence integrated into the genome DNA 10 includes two transposase-binding sequences 41, and an optional base sequence 45 is included therebetween. The base sequence 45 is formed by the fill-in reaction.

The base sequence shown in FIG. 5(c) is a non-targeted by-product and is integrated into any part of the genome DNA 10, not limited to a site adjacent to the binding region 11. However, the base sequence shown in FIG. 5(c) does not have a desired base sequence (in this example, the base sequence to which the identification sequence 43 is linked downstream the T7 promotor sequence 42). For this reason, influence on targeted analysis can be excluded.

By the above step, it is possible to integrate the DNA fragment of a desired base sequence into a site adjacent to the binding region of the DNA-binding protein bound to a DNA molecule.

(Specific Binding Substance)

In the ChILT method, examples of the specific binding substance include antibodies, antibody fragments, aptamers, and the like. An antibody can be manufactured by immunizing a target substance or a fragment thereof as an antigen to an animal such as mouse. Alternatively, for example, an antibody can be manufactured by screening of a phage library. Examples of the antibody fragment include Fv, Fab, scFv, and the like. The antibody may be a monoclonal antibody, or may be a polyclonal antibody. In addition, the antibody may be a commercially available antibody.

The aptamer is a substance having a specific binding function to a target substance. Examples of the aptamer include a nucleic acid aptamer, a peptide aptamer, and the like. The nucleic acid aptamer having a specific binding function to a target substance can be selected by a method of systematic evolution of ligand by exponential enrichment (SELEX), for example. In addition, the peptide aptamer having a specific binding function to a target substance can be selected by a two-hybrid method using yeast, for example.

(Desired Base Sequence)

In addition, in the examples of FIG. 1C to FIG. 5, a desired base sequence integrated into the genome DNA 10 is a base sequence to which the identification sequence 43 is linked downstream the T7 promotor sequence 42, but the desired base sequence is not limited thereto. For example, as the desired base sequence, other promotor sequences such as SP6 promotor sequence may be used instead of the T7 promotor sequence 42. Alternatively, the desired base sequence may be made only of a promotor sequence, or the desired base sequence may be made only of an identification sequence. In addition, the identification sequence is not particularly limited as long as the identification sequence is a base sequence having a probabilistically low appearance frequency. For example, an optional base sequence of approximately 4 to 20 bases can be used.

A length of the desired base sequence integrated into the genome DNA 10 may be a base of 20 to 500, for example, may be a base of 20 to 200, for example, and may be a base of 20 to 100, for example.

In addition, in the examples of FIG. 1C to FIG. 5, each element (T7 promotor sequence 42, identification sequence 43, and transposase-binding sequence 41) constituting the DNA fragment 40 is adjacent one another, but there may exist a space of an optional base sequence between elements. In addition, the order of each element is not limited to that shown in FIG. 1C to FIG. 5 and may be appropriately changed depending on the necessity, and additional elements may be added thereto.

In addition, the DNA fragment 40 may be one chain, or may be two chains. Here, in a case where the transposase-binding sequence 41 is required to be two-chain DNA, depending on the features of the transposase to be used, at least the transposase-binding sequence 41 is required to be two chains.

By the reaction, a DNA fragment of a desired base sequence is integrated into a site adjacent to a binding region of a DNA-binding protein using an immobilized cell specimen as a sample, cells are dissected by laser microdissection and collected, and analysis to be described later can be performed at single-cell level.

(Analysis Using DNA Fragment Integrated by ChILT Method)

The ChILT method may further include a step of performing gene amplification of DNA 10 having the desired base sequence (base sequence to which the identification sequence 43 is linked downstream the T7 promotor sequence 42 as a starting point in the examples of FIG. 1C to FIG. 5) to obtain an amplification product and a step of analyzing a base sequence of the amplification product. Thereby, it is possible to analyze a position on a genome into which the desired DNA fragment is integrated.

(Gene Amplification)

The gene amplifications are, for example, transcription using PCR combining a complementary primer and a random primer with the integrated base sequence, polymerase (RNA polymerase, DNA-dependent DNA polymerase, and the like). In the present specification, "gene amplification using a desired base sequence as a starting point" means gene amplification of the genome DNA 10 using part or all of the desired base sequence integrated into a site located adjacent to the binding region 11.

For example, in the examples of FIG. 1C to FIG. 5, the T7 promotor sequence 42 is included in the base sequence integrated into the genome DNA 10. Here, "gene amplification using a desired base sequence as a starting point" may be transcription of the genome DNA 10 downstream the T7 promotor sequence 42 to RNA by acting and transcribing the T7 polymerase to the genome DNA 10.

Alternatively, "gene amplification using a desired base sequence as a starting point" may be gene amplification of a base sequence of the genome DNA 10 adjacent to the binding region 11 by performing PCR combining a primer having a complementary base sequence and a random primer with a part or all of the integrated base sequence, using the genome DNA 10 as a template.

That is, in the ChILT method, the integrated base sequence includes a promotor sequence, and gene amplification may be gene amplification by bringing RNA polymerase into the promotor sequence into contact, transcribing DNA downstream the promotor sequence, and generating RNA. As described above, since the base sequence shown in FIG. 5(c) does not have the T7 promotor sequence 42, this gene amplification (transcription) does not occur even when the T7 polymerase acts.

Alternatively, gene amplification may be performed by PCR using the integrated desired base sequence and the like. As described above, since the base sequence shown in FIG. 5(c) does not have the desired base sequence (base sequence to which the identification sequence 43 is bound downstream the T7 promotor sequence 42), gene amplification is not performed even when PCR reaction using the base sequence is performed.

(Identification Sequence)

FIG. 6(a) is a view showing a state in which the T7 polymerase is acted in DNA 10 shown in FIG. 4 or FIG. 5(a), and DNA 10 downstream the T7 promotor sequence 42 is transcribed to RNA 60. In addition, FIG. 6(b) is a view in which the T7 polymerase is acted in DNA 10 shown in FIG. 5(b), and DNA 10 downstream the T7 promotor sequence 42 is transcribed to RNA 60.

In the examples of FIGS. 6(a) and 6(b), the identification sequence 43 is introduced downstream the T7 promotor sequence 42. That is, in the ChILT method, the desired base sequence may further include an identification sequence downstream the promotor sequence.

In the examples of FIGS. 6(a) and 6(b), since the identification sequence 43 is introduced downstream the T7 promotor sequence 42, RNA 60 includes a complementary chain 43' of the identification sequence 43 and a complementary chain 10' of DNA 10 downstream the identification sequence 43.

If the T7 RNA polymerase is acted in a genome DNA, there is a case where RNA is transcribed from a domain other than the T7 promotor sequence 42 integrated by the reaction. With respect to this, if the identification sequence 43 exists, it is possible to identify RNA to which the integrated T7 promotor sequence 42 is transcribed as a starting point and other RNA. That is, it can be determined that the RNA 60 having the complementary chain 43' of the identification sequence 43 is RNA to which the integrated T7 promotor sequence 42 is transcribed as a starting point.

In addition, as described above, in the ChILT method, it is possible to simultaneously perform analysis using a specific binding substance to a plurality of DNA-binding proteins. Here, by introducing different identification sequences 43 to the DNA fragment 40 integrated into DNA 10 using each specific binding substance, it is also possible to identify whether RNA is RNA transcribed from a site adjacent to the binding region of any DNA-binding protein.

Subsequently, by analyzing the base sequence of the transcribed RNA 60, it is possible to specify a position on the genome to which the DNA-binding protein is bound. Analysis of the base sequence of RNA 60 may be performed by a next-generation sequencer, for example, and may be performed by hybridization with DNA array.

Figure 6:
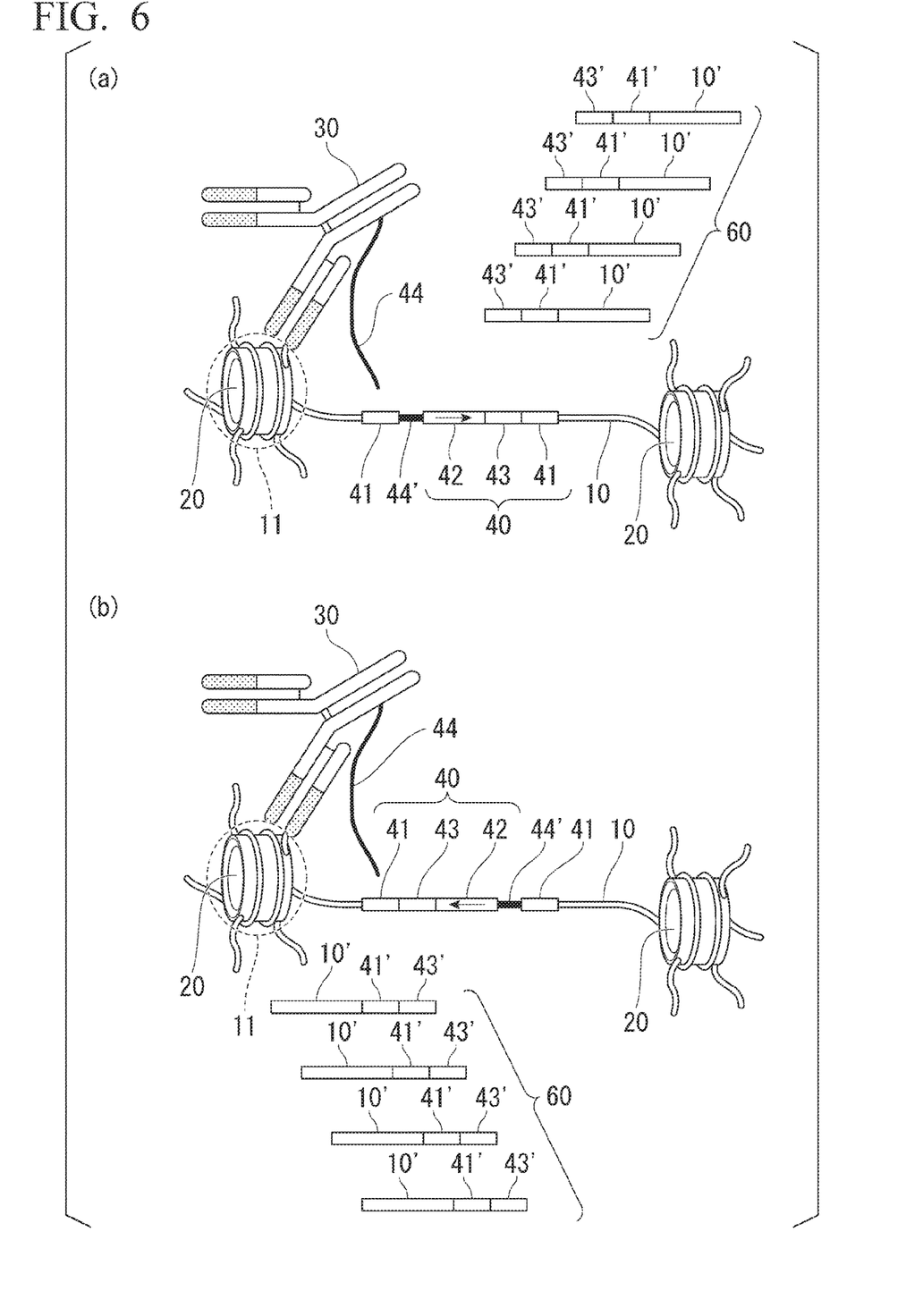
FIGS. 6(a) and 6(b) are schematic views showing the ChILT method.

In the examples of the FIGS. 6(a) and 6(b), domains transcribed to the RNA 60 are different from each other, but in any example, the RNA 60 is RNA transcribed from a site adjacent to the binding region 11. Therefore, by analyzing the base sequence of the RNA 60, it is possible to specify a position on the genome of the binding region of the DNA-binding protein (in the examples of FIGS. 1 to 6, the histone 20). That is, a direction in which the desired base sequence is integrated does not affect the analysis result.

[Bonded Body]

In the First Embodiment, the present invention provides a bonded body between a DNA fragment including a transposase-binding sequence and a desired base sequence and a specific binding substance to a DNA-binding protein or a specific binding substance to the specific binding substance.

The bonded body of the present embodiment can be used for integrating the desired base sequence into a site adjacent to the binding region of the DNA-binding protein bound to the DNA molecule.

In the bonded body of the present embodiment, the transposase-binding sequence, the desired base sequence, the specific binding substance are the same as above. That is, the desired base sequence may include a promotor sequence. In addition, the desired base sequence further includes an identification sequence downstream the promotor sequence.

In the bonded body of the present embodiment, the DNA fragment is preferably bound to a specific binding substance to a DNA-binding protein or a specific binding substance to the specific binding substance via a linker. The linker is the same as above.

In the bonded body of the present embodiment. "the bonded body between the DNA fragment and the specific binding substance to a DNA-binding protein" means a bonded body in which the DNA fragment is bound to a primary antibody", for example. That is, the bonded body means a bonded body in which the DNA fragment is directly bound to the specific binding substance to a DNA-binding protein.

In addition, in the bonded body of the present embodiment, "the bonded body between the DNA-binding protein and a specific binding substance to the specific binding substance to the DNA fragment" means a bonded body in which the DNA fragment is bound to a secondary antibody, for example. That is, in the present embodiment, the DNA fragment is not bound to the specific binding substance to a DNA-binding protein, but is bound to the specific binding substance bound to the specific binding substance to a DNA-binding protein. More specifically, for example, in a case where the specific binding substance to a DNA-binding protein is a mouse IgG, a bonded body between the DNA fragment and the anti-mouse IgG antibody and the like are exemplified.

The number of the DNA fragments per one molecule of the specific binding substance is not particularly limited, but may be 1 to 10, for example.

A method for binding the DNA fragment to the specific binding substance is not particularly limited, and, for example, a chemical crosslinking agent having a succinimide group, a maleimide group, and the like may be used for binding. For example, when binding an amino group to a 5' terminal of the DNA fragment, the method includes covalent binding between the amino group and a functional group such as amino group existing in the specific binding substance and a carboxy group with an appropriate chemical crosslinking agent. Alternatively, for example, the DNA fragment may be bound to the specific binding substance using binding between avidin and biotin.

EXAMPLES

Next, the present invention will be further described in detail referring to examples, but the present invention is not particularly limited to the following examples.

Experimental Example 1

By ChIP-Seq analysis which is a conventional method, a binding position on a genome DNA of lysine tetratrimethylated-modified histone H3 (H3K4me3) which is a DNA-binding protein was analyzed using approximately 1,000 mouse skeletal myoblasts.

(Preparation of Soluble Chromatin Fraction)

Mouse skeletal myoblasts with numbers of 1,000 were suspended in 1 mL of a medium, and put into 1.5 mL of a siliconized tube. Subsequently, 100 µL of an immobilized solution (37% formaldehyde) was added thereto, and the cell sample was incubated at room temperature for 5 minutes, and thus the DNA and the DNA-binding protein were crosslinked.

Subsequently, 100 µL of 1 M glysine aqueous solution was added thereto, and the sample was stirred at room temperature for 5 minutes. Thereby, glysine and remaining formaldehyde were reacted with each other, and crosslinking reaction was stopped. Subsequently, centrifugation was performed at 3,000 rpm, at 4° C. for 5 minutes, a supernatant was removed, and cells were further washed two times with a phosphate buffer solution (PBS).

Subsequently, 2 mL of ChIP buffer (10 mM Tris-HCl (pH 8.0), 200 mM KCl, 1 mM $CaCl_2$, 0.5% NP40, PMSF, aprotinin, leupeptin) was added to suspend cells, and the cell suspension was incubated on ice for 10 minutes.

Subsequently, DNA fragmentation was performed by ultrasonication using an ultrasonic cell crushing apparatus while cooling with iced water.

Subsequently, the sample was digested with micrococcal nuclease at 37° C. for 40 minutes. Subsequently, EDTA was added to the sample at final concentration of 10 mM to stop the reaction. Subsequently, centrifugation was performed at 15,000×g at 4° C., and supernatant was collected in 2 mL of the siliconized tube. Subsequently, the ChIP buffer was added to perform dilution, and a soluble chromatin fraction was obtained.

(Immunoprecipitation)

An antibody complex solution obtained by reacting 2 µg of a rabbit anti-mouse IgG antibody and 2 µg of a mouse anti-H3K4me3 antibody in advance and magnetic beads (Dynabeads M-280) to which 20 µL of a goat anti-rabbit IgG antibody were bound to the soluble chromatin fraction, and the resultant product was stirred at 4° C. overnight with rotation.

Subsequently, a reaction solution was set in a magnetic stand, and the sample was incubated for 1 minute to collect the magnetic beads. Subsequently, the magnetic beads were washed three times with the ChIP buffer, washed three times with a washing buffer (10 mM Tris-HCl (pH 8.0), 500 mM KCl, 1 mM $CaCl_2$, 0.5% NP40), and washed three times with 1×TE (10 mM Tris-HCl (pH 8.0), 1 mM EDTA (pH 8.0)).

(Purification of DNA)

100 µL of a ChIP elution buffer (50 mM Tris-HCl (pH 8.0), 10 mM EDTA, 1% SDS) was added thereto, the magnetic beads was suspended using a vortex mixer, and 5 µL of 5M NaCl was further added thereto. Subsequently, heating was performed at 65° C. for 4 hours, and crosslinking between a DNA and a DNA-binding protein was released.

Subsequently, 0.5 µL of 10 mg/mL RNaseA was added thereto. After stirring with vortex mixer, the sample was incubated at 37° C. for 30 minutes. Subsequently, 1 µL of 10 mg/mL proteinase K was added thereto, and the sample was stirred using the vortex mixer to perform incubating at 50° C. for 1 hour. Subsequently, DNA was purified using a PCR purification kit (Qiagen, Inc.).

(Analysis of Base Sequence)

Subsequently, the base sequence of the collected DNA was analyzed by the next-generation sequencer.

(Result)

Figure 7:
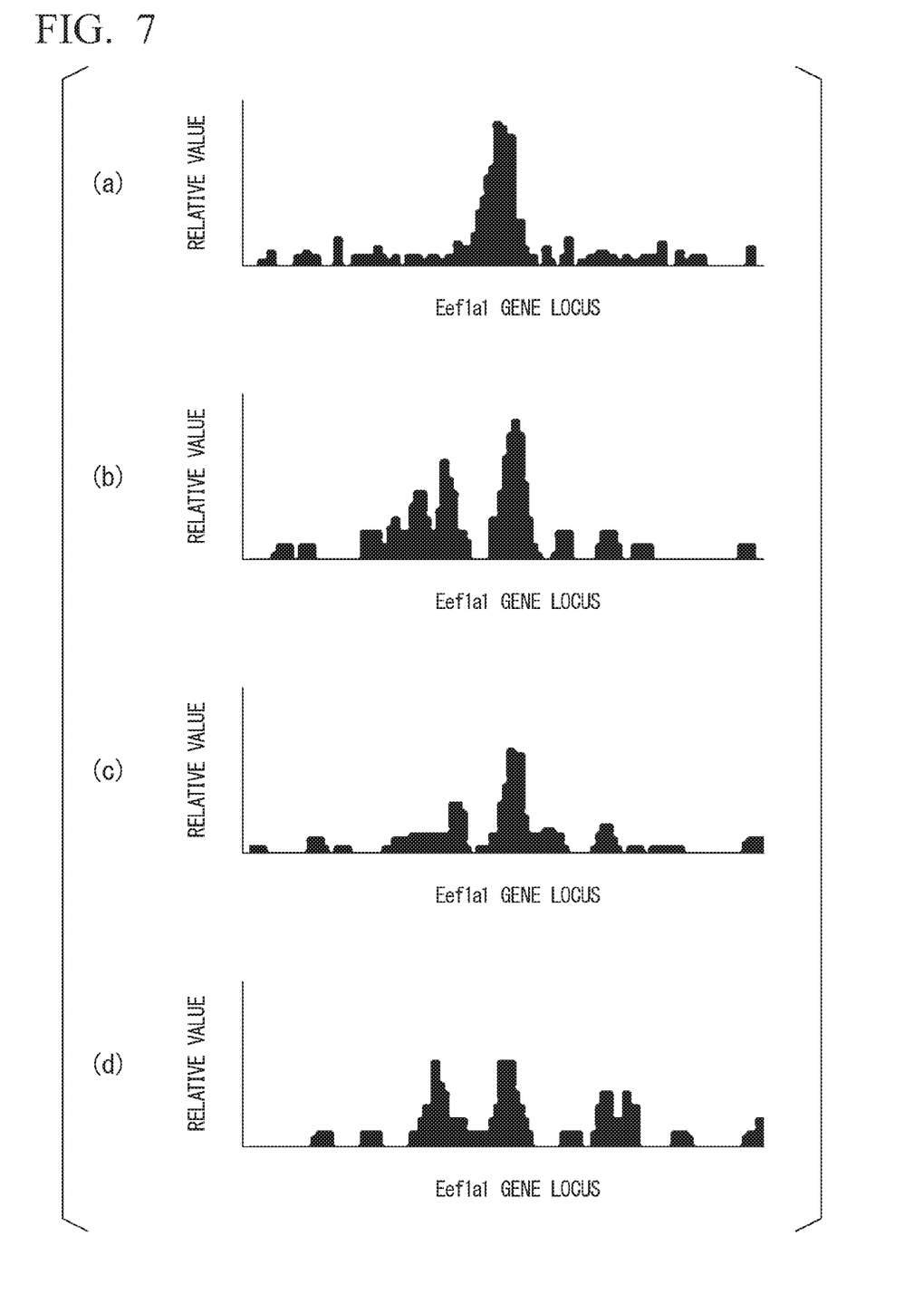
FIGS. 7(a) to 7(d) are graphs showing a result of Experimental Examples 1 and 2.

FIG. 7(a) is a graph showing a result obtained by mapping binding of the H3K4me3 to an Eef1a1 gene locus using approximately 1,000 cells by the ChIP-Seq analysis which is a conventional method.

Experimental Example 2

By the ChILT method, a binding position on a genome DNA of lysine tetrtriamethylated-modified histone H3

(H3K4me3) which is a DNA-binding protein was analyzed at single-cell level using mouse skeletal myoblasts.

(Immobilization of Cells)

First, mouse skeletal myoblasts were plated on a slide glass. Subsequently, after culturing for 16 hours, the medium was removed, and washed with PBS. Subsequently, 1% paraformaldehyde solution was added thereto, the sample was incubated at room temperature for 5 minutes. Thus the cells were fixed, and then washed with PBS.

(Bringing DNA Fragment Close to H3K4Me3-Binding Region)

Subsequently, a blocking agent (product name "Blocking One-P". Nacalai Tesque Corporation) was added to the fixed cell sample. After incubation at room temperature for 10 minutes, the sample was washed with PBS. Subsequently, an antibody complex (obtained by reacting 2 µg/mL anti-H3K4me3 antibody with a nucleic acid-labeled secondary antibody) diluted with 0.1×Blocking One-P was added thereto, reacted at 37° C. for 2 hours, and then washed with PBS. As a result, the DNA fragment labeled to the nucleic acid-labeled secondary antibody and a H3K4me3-binding region on a genome DNA were brought close to each other.

Here, the DNA fragment labeled to the nucleic acid-labeled secondary antibody was obtained by annealing a DNA fragment made of a base sequence described in the Seq ID No. 1 and a DNA fragment made of a base sequence described in the Seq ID No. 2.

In the base sequence described in the Seq ID No. 1, the $49^{th}$ to the $67^{th}$ base sequences were binding sequences of TN5 transposase, the $7^{th}$ to the $26^{th}$ base sequences were T7 promotor sequences, the $27^{th}$ to the $34^{th}$ base sequences were identification sequences, and the $1^{st}$ to the $6^{th}$ base sequences were base sequences of a part of a linker.

In addition, the DNA fragment having the base sequence described in the Seq ID No. 2 is a DNA fragment including the $49^{th}$ to the $67^{th}$ base sequences and complementary base sequences in the base sequences described in the Seq ID No. 1, and the base sequence of TN5 transposase which is a double stranded DNA was formed by annealing the DNA fragment with the DNA fragment having the base sequence described in the Seq ID No. 1.

(Binding of Transposase)

Subsequently, TN5 transposase was added to the sample at a concentration of 85 µg/mL, and incubated at room temperature for 10 minutes. Thereby, transposase was bound to the transposase-binding sequence in the DNA fragment labeled to the nucleic acid-labeled secondary antibody.

(Activation of Transposase and Integration of Desired Base Sequence)

Subsequently, a free DNA fragment (hereinafter, referred to as "oligo3-4") having a transposase-binding sequence was added to the sample, reacted at room temperature for 1 hour, and then washed with PBS. The oligo3-4 was obtained by annealing a DNA fragment having a base sequence described in the Seq ID No. 3 and a DNA fragment having a base sequence described in the Seq ID No. 4. A double stranded DNA domain of the oligo3-4 was a binding sequence of TN5 transposase.

Subsequently, the sample was washed with 1×TN5 dialysis buffer (50 mM HEPES-KOH (pH 7.2), 0.1 M NaCl, 0.1 mM EDTA, 1 mM DTT, 0.1% Triton X-100, 10% glycerol).

Subsequently, 1×TAPS-DMF buffer (10 mM TAPS-NaOH (pH 8.5), 5 mM $MgCl_2$, 10% N,N-dimethylformaldehyde) was added to the sample, and the sample was incubated at 37° C. for 1 hour. Thereby, transposase bound to the DNA fragment labeled to the nucleic acid-labeled secondary antibody was activated, and thus the DNA fragment was integrated into a site adjacent to a H3K4me3-binding region of the genome DNA.

Subsequently, a 1% sodium dodecyl sulfate solution was added thereto. After incubation at room temperature for 10 minutes, the sample was washed with PBS. Thereby, transposase was deactivated and removed.

Subsequently, the sample was washed with 1×T4DNA ligase reaction buffer, added with a fill-in reaction solution (T4DNA ligase reaction buffer, dNTPmix, T4DNA ligase 1, T4DNA polymerase 1), and reacted at room temperature for 30 minutes. Thereby, the DNA fragment labeled to the nucleic acid-labeled secondary antibody was reliably integrated into a site adjacent to a H3K4me3-binding region of the genome DNA.

Subsequently, a 1% sodium dodecyl sulfate solution was added thereto. After incubation at room temperature for 10 minutes, the sample was washed with PBS. Thereby, T4DNA ligase and T4DNA polymerase I were deactivated and removed.

(Dissection of 1 Cell)

Subsequently, target cells were dissected one by one by laser microdissection, and each of the cells was transferred in a microtube.

(Gene Amplification)

Here, as gene amplification, transcription was performed using T7RNA polymerase. First, each of the dissected cells was washed with a 1×T7RNA polymerase buffer. Subsequently, an in-vitro transcription solution (T7RNA polymerase buffer, ATP, CTP, GTP, UTP, RNase inhibitor, T7RNA polymerase) was added thereto, and reacted at 37° C. for 16 hours. Thereby, the genome DNA was transcribed, with the T7RNA promotor sequence included in the integrated DNA fragment as a starting point.

Subsequently, DNaseI was added thereto, and the resultant product was reacted at 37° C. for 30 minutes. Thereby, DNA included in the collected cells was analyzed. Subsequently, the transcribed RNA was purified using RNeasy MinElute Cleanup Kit (Qiagen, Inc.).

(Base Sequence Analysis of Collected RNA)

Subsequently, the purified RNA was reverse-transcribed to prepare cDNA, and the base sequence was analyzed using a next-generation sequencer for genome mapping.

(Result)

FIGS. 7(b) to 7(d) are respectively graphs showing a representative result obtained by analyzing binding of the H3K4me3 to the Eef1a1 gene locus at single-cell level by the ChILT method.

As a result, as shown in FIGS. 7(b) to 7(d), it was clarified that there is a difference in binding of the H3K4me3 to the Eef1a1 gene locus depending on each cell. Such a result cannot be detected by the ChIP-Seq analysis using 1,000 cells of FIG. 7(a), but can be detected only by analyzing binding of a DNA and a DNA-binding protein at single-cell level.

Experimental Example 3

Binding of various DNA-binding proteins on a genome DNA was analyzed at single-cell level by the ChILT method. Mouse skeletal myoblasts were used as the cell. In addition, as a primary antibody, an anti-DNA-binding protein antibody shown in the following Table 1 was used. In addition, as a secondary antibody, an anti-mouse IgG antibody or an anti-rabbit IgG antibody labeled with the same DNA fragment as that used in Experimental Example 2 was used.

TABLE 1

| Primary antibody | Description of antibody |
| --- | --- |
| rH3K27me3 | Rabbit IgG antibody to lysine 27 trimethylated-modified histone H3 |
| rCTCF | Rabbit IgG antibody to CTCF protein |
| mH3K4me3 | Mouse IgG antibody to lysine 4 trimethylated-modified histone H3 |
| mH3K27me3 | Mouse IgG antibody to lysine 27 trimethylated-modified histone H3 |
| mH3K27ac | Mouse IgG antibody to lysine 27 acetylated-modified histone H3 |

(Immobilization of Cells)

Similar to Experimental Example 2, mouse skeletal myoblasts on a slide glass were cultured and immobilized, and washed with PBS.

(Reaction of Antibody Complex)

Subsequently, similar to Experimental Example 2, a blocking agent (product name "Blocking One-P", Nacalai Tesque Corporation) was added to an inunobilized cell sample. After incubation at room temperature for 10 minutes, the sample was washed with PBS. Subsequently, an antibody complex distilled with 0.1×Blocking One-P (obtained by reacting a primary antibody with a nucleic acid labeling secondary antibody in advance) was added thereto, reacted at 37° C. for 2 hours, and then washed with PBS.

The antibody complex was prepared by reacting a nucleic acid labeling mouse antibody with the secondary antibody in a case where the primary antibody was a mouse antibody. In addition, the antibody complex was prepared by reacting a nucleic acid labeling rabbit antibody with the secondary antibody in a case where the primary antibody was a rabbit antibody.

In addition, as a negative control, a sample obtained by reacting only the nucleic acid labeling anti-mouse IgG antibody or only the nucleic acid labeling anti-rabbit IgG antibody was also prepared. That is, a sample obtained by not reacting a primary antibody was prepared as a negative control. After that, binding of transposase, activation of transposase, and integration of a desired base sequence were performed in the same manner as that of Experimental Example 2.

(Dissection of 1 Cell)

Subsequently, target cells were dissected one by one by laser microdissection, and each of the cells was transferred in a microtube.

(Gene Amplification and Base Sequence Analysis)

Transcription was performed on each of the collected cells by T7RNA polymerase in the same manner as that of Experimental Example 2, and the transcribed RNA was purified. Subsequently, the purified RNA was reverse-transcribed to prepare cDNA, and the base sequence was analyzed using a next-generation sequencer, and mapped on a genome.

(Result)

Figure 8A:
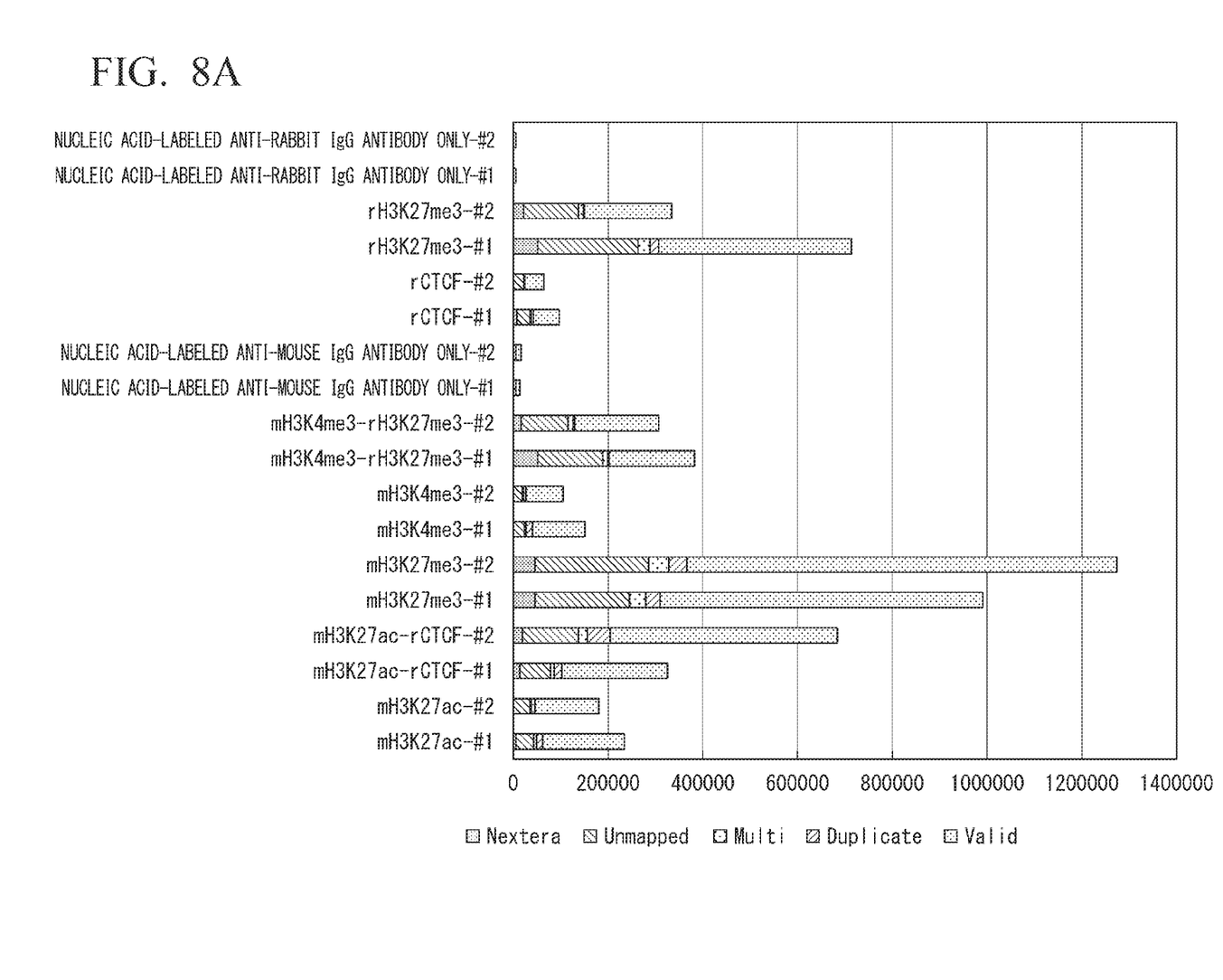
FIG. 8A is a graph showing a result of Experimental Example 3.

FIG. 8A is a graph showing a result obtained by analyzing and mapping binding of the DNA-binding protein at single-cell level by the ChILT method using various primary antibodies shown in Table 1. Two cells were analyzed for each antibody complex.

In FIG. 8A, the axis of abscissas of the graph represents the number of leads obtained by the next-generation sequencer. In addition, "Valid" represents leads effectively mapped on a genome, "Duplicate" represents leads with two leads mapped at the same position on the genome, "Multi" represents leads with three leads mapped at the same position on the genome, "Unmapped" represents leads unmapped on the genome, and "Nextera" represents leas derived from a library used in the base sequence analysis.

FIG. 8A represents, for example, that "rH3K27me3" is a result of reacting a complex between the rH3K27me3 antibody and the nucleic acid labeling anti-rabbit IgG antibody, and is as follows. In addition, for example, FIG. 8A represents that "mH3K4me3-rH3K27mc3" is a result of reacting a complex between the mH3K4me3 antibody and the nucleic acid labeling anti-mouse IgG antibody and a complex between the rH3K27me3 antibody and the nucleic acid labeling anti-rabbit IgG antibody simultaneously, and is as follows. In addition, "#1" and "#2" respectively represent a result of a first cell and a result of a second cell of the analyzed two cells.

As a result, it was checked that in the negative control not using the primary antibody, almost no leads were obtained, and leads were obtained depending on the reaction of the primary antibody. In addition, it was checked that leads were obtained depending on the amount of histone-modification or transcription factors existing in the cell.

Figure 8B:
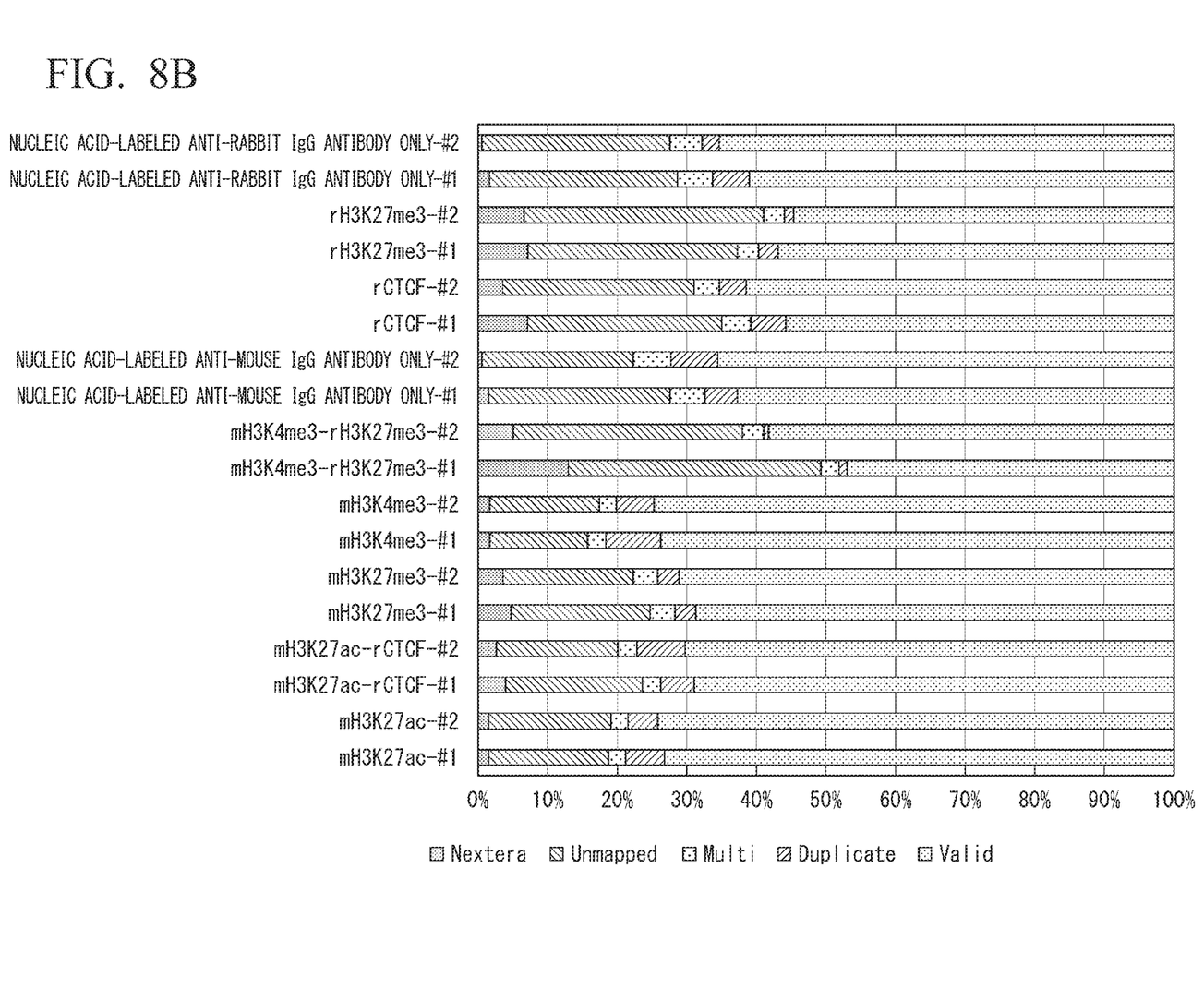
FIG. 8B is a graph showing a result of Experimental Example 3.

FIG. 8B is a graph of modifying the axis of abscissas in FIG. 8A to the existence ratio of each lead of "Valid". "Duplicate". "Multi", "Unmapped", and "Nextera". As a result, it was clarified that it is possible to obtain approximately 50% to 85% of effective leads by the ChILT method using the nucleic acid labeling anti-mouse IgG antibody or the nucleic acid labeling anti-rabbit IgG antibody.

INDUSTRIAL APPLICABILITY

According to the present invention, it is possible to provide a technique capable of analyzing binding between a protein and a specific genome domain without performing immunoprecipitation. Therefore, for example, it is possible to analyze binding of a protein such as insoluble proteins, of which immunoprecipitation is difficult to be performed, to DNA. In addition, analysis in which a sample is a small number of cells also becomes easy.

REFERENCE SIGNS LIST

10 Genome DNA

10' Complementary chain of genome DNA 10

11 Binding region

20 Histone

30 Specific binding substance

40 DNA fragment

41 Transposase-binding sequence

41' Complementary chain of transposase-binding sequence 41

42 T7 promotor sequence

43 Identification sequence

43' Complementary chain of identification sequence 43

44 Linker

44' Base sequence derived from a part of linker 44

45 Optional sequence

50 Transposase

60 RNA

S Cell specimen

The invention claimed is:

1. A method for integrating a DNA fragment of a desired base sequence into a site located adjacent to a binding region of a DNA-binding protein bound to a DNA molecule of a paraformaldehyde or formaldehyde-immobilized cell, the method comprising:
   (i) bringing the DNA fragment having a base sequence including a transposase-binding sequence and the desired base sequence close to the binding region using a specific binding substance to the DNA-binding protein in situ;
   (ii) binding a transposase to the transposase-binding sequence; and
   (iii) activating the transposase such that the DNA fragment of the desired base sequence is integrated into the site located adjacent to the binding region.

2. The method according to claim 1, further comprising:
   performing gene amplification of the DNA molecule using the desired base sequence as a starting point to obtain an amplification product; and
   analyzing a base sequence of the amplification product.

3. The method according to claim 2,
   wherein the desired base sequence includes a promotor sequence, and
   wherein the gene amplification is performed by bringing RNA polymerase into contact with the promotor sequence, and transcribing DNA downstream the promotor sequence to generate RNA.

4. The method according to claim 3,
   wherein the desired base sequence further includes an identification sequence downstream the promotor sequence.

5. A bonded body having a DNA fragment for integration into genomic DNA in a cell, the bonded body comprising (i) a base nucleotide sequence including a transposase-binding sequence and a desired base sequence, and (ii) (a) a primary antibody to a DNA-binding protein or (b) a secondary antibody to a primary antibody to a DNA-binding protein, wherein (i) the bonded body is capable of bringing the base nucleotide sequence close to a binding region of a DNA-binding protein in situ and (ii) the bonded body does not include a transposase.

6. The bonded body according to claim 5,
wherein the desired base sequence includes a promotor sequence.

7. The bonded body according to claim 6,
wherein the desired base sequence further includes an identification sequence downstream the promotor sequence.

8. A method for integrating a DNA fragment of a desired base sequence into a site located adjacent to a binding region of a DNA-binding protein bound to a DNA molecule of a paraformaldehyde or formaldehyde-immobilized cell, the method comprising:
  (i) bringing a bonded body according to claim 5 close to the binding region using (a) the primary antibody or (b) the secondary antibody;
  (ii) binding a transposase to the transposase-binding sequence of the bonded body; and
  (iii) activating the transposase such that the DNA fragment of the desired base sequence is integrated into the site located adjacent to the binding region.

* * * * *

SEQUENCE LISTING

```
<160> NUMBER OF SEQ ID NOS: 4

<210> SEQ ID NO 1
<211> LENGTH: 67
<212> TYPE: DNA
<213> ORGANISM: Artificial Sequence
<220> FEATURE:
<223> OTHER INFORMATION: A DNA fragment for ChILT method

<400> SEQUENCE: 1
atgcattaat acgactcact atagggtaga tcgctcgtcg gcagcgtcag atgtgtataa      60
gagacag                                                               67

<210> SEQ ID NO 2
<211> LENGTH: 19
<212> TYPE: DNA
<213> ORGANISM: Artificial Sequence
<220> FEATURE:
<223> OTHER INFORMATION: A DNA fragment for ChILT method

<400> SEQUENCE: 2
ctgtctctta tacacatct                                                  19

<210> SEQ ID NO 3
<211> LENGTH: 34
<212> TYPE: DNA
<213> ORGANISM: Artificial Sequence
<220> FEATURE:
<223> OTHER INFORMATION: A DNA fragment for ChILT method

<400> SEQUENCE: 3
gtctcgtggg ctcggagatg tgtataagag acag                                 34

<210> SEQ ID NO 4
<211> LENGTH: 19
<212> TYPE: DNA
<213> ORGANISM: Artificial Sequence
<220> FEATURE:
<223> OTHER INFORMATION: A DNA fragment for ChILT method

<400> SEQUENCE: 4
ctgtctctta tacacatct                                                  19
```